(12) United States Patent
Sugiyama et al.

(10) Patent No.: US 7,535,568 B2
(45) Date of Patent: May 19, 2009

(54) BIOCHIP, BIOCHIP READER AND BIOCHIP READING METHOD

(75) Inventors: Yumiko Sugiyama, Musashino (JP); Takeo Tanaami, Musashino (JP)

(73) Assignee: Yokogawa Electric Corporation, Musashino-shi (JP)

( * ) Notice: Subject to any disclaimer, the term of this patent is extended or adjusted under 35 U.S.C. 154(b) by 0 days.

(21) Appl. No.: 11/524,430

(22) Filed: Sep. 21, 2006

(65) Prior Publication Data

US 2007/0070344 A1 Mar. 29, 2007

(30) Foreign Application Priority Data

Sep. 27, 2005 (JP) .............................. 2005-279503

(51) Int. Cl.
*G01N 21/64* (2006.01)
(52) U.S. Cl. .................... 356/417; 356/318; 250/458.1; 436/172
(58) Field of Classification Search ................. 356/317, 356/318, 417, 401
See application file for complete search history.

(56) References Cited

U.S. PATENT DOCUMENTS 6,537,801 B1 * 3/2003 Ida et al. ................... 435/287.2

2004/0224318 A1 11/2004 Mahant et al.

FOREIGN PATENT DOCUMENTS

| WO | WO 01/35099 A1 | 5/2001 |
| WO | WO 03/003021 A1 | 1/2003 |
| WO | WO 03/100474 A2 * | 12/2003 |

OTHER PUBLICATIONS

T. Makino et al., "DNA Analysis and Optical Technique" Optical Technique in Life Science, Journal of "Optics" vol. 28, No. 10 (1999), (Corp.) Japan Society of Applied Physics, section meeting, Optical Society of Japan, 1999, pp. 549-552.
European Search Report dated Feb. 12, 2007, issued in corresponding European patent application No. 06017987.6.

* cited by examiner

*Primary Examiner*—F. L Evans
(74) *Attorney, Agent, or Firm*—Westerman, Hattori, Daniels & Adrian, LLP.

(57) ABSTRACT

A biochip for implementing analysis on the basis of the distribution of a quantity of light of fluorescent light generated at sites disposed thereon, the biochip having, markers formed thereon and defined previously in a positional relationship relative to the sites; and a processor for recognizing positions of the sites on the biochip on the basis of the positions of the markers, wherein the markers are formed of at least one of dyes, pigment, metal colloid bonded to biopolymer, dyes bonded to biopolymer, and pigment bonded to biopolymer.

3 Claims, 3 Drawing Sheets

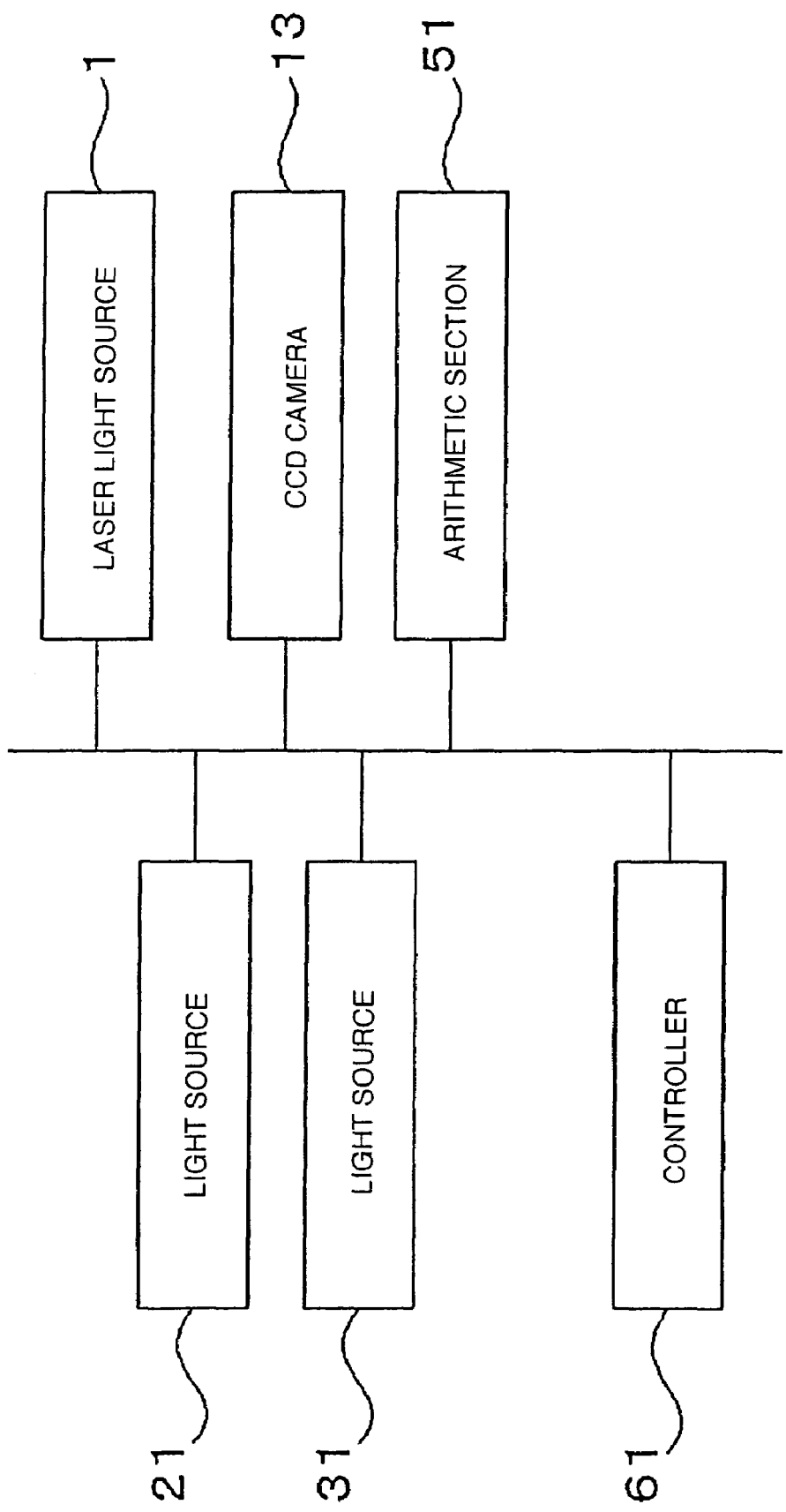

BIOCHIP, BIOCHIP READER AND BIOCHIP READING METHOD

FIELD OF THE INVENTION

The invention relates to a biochip for implementing analysis on the basis of distribution of a quantity of fluorescent light generated at a site, a biochip reader and a biochip reading method.

BACKGROUND OF THE INVENTION

A method of using a biochip has been known as a method for fixedly attaching biopolymer such as DNAs. In the case of fixedly attaching, for example, DNAs, a DNA probe having a known base sequence is fixedly attached to respective sites of a biochip, then target DNAs having a complementary base sequence by hybridization are bonded to respective sites. By marking the target DNAs bonded by hybridization to respective sites with fluorescent molecules, the amount of bonding of the target DNAs can be recognized as a quantity of fluorescence light.

[Non-patent document: Optical technique "DNA analysis and optical technique" optical technique in life science, Journal of "optics" edited by Toru Makino and kyoichi Kano, Volume 28, No. 10 (1999), (Corp.) Japan Society of Applied Physics, section meeting, Optical Society of Japan, 1999, pp 549-552

SUMMARY OF THE INVENTION

A quantity of light is measured by use of a dedicated reader. It is necessary to detect the positions of the sites so as to measure quantities of light of respective sites. However, since the site formed by spotting with liquid is transparent, it is impossible to detect positions of respective sites by photograph. Although it is possible to detect the positions of respective sites utilizing fluorescent light of respective sites to which hybridization is applied, if the fluorescent light of the site is dark, it is difficult to identify the positions of respective sites.

It is an object of the invention to provide a biochip and so forth capable of detecting the positions of the respective sites with ease.

The biochip of the invention for implementing analysis on the basis of the distribution of a quantity of light of fluorescent light generated at sites disposed thereon has markers formed thereon and defined previously in a positional relationship relative to the sites.

The sites and the markers may be formed by the same process with the same device.

The markers are formed of at least one of dyes, pigment, metal colloid bonded to biopolymer, dyes bonded to biopolymer, and pigment bonded to biopolymer.

A biochip reader for implementing analysis on the basis of the distribution of a quantity of light of fluorescent light generated at sites on a biochip comprises a marker position detection means for detecting positions of markers formed on the biochip and defined previously in a positional relationship relative to the sites, and a recognition means for recognizing positions of the sites on the biochip on the basis of the positions of the markers thus detected.

A biochip reading method of the invention for implementing analysis on the basis of the distribution of a quantity of light of fluorescent light generated at sites on a biochip comprises a step of detecting markers formed on the biochip and defined previously in a positional relationship relative to the sites, and a step of recognizing positions of the sites on the biochip on the basis of the positions of the markers thus detected.

According to the biochip of the invention, since the markers are formed on the biochip and defined in positional relationship relative to the sites, the positions of the sites can be easily recognized on the basis of the positions of the markers.

BRIEF DESCRIPTION OF THE DRAWINGS

FIG. 3 is block diagram showing a configuration of a control system of the biochip reader according to the present embodiment.

PREFERRED EMBODIMENT OF THE INVENTION

Figure 1:
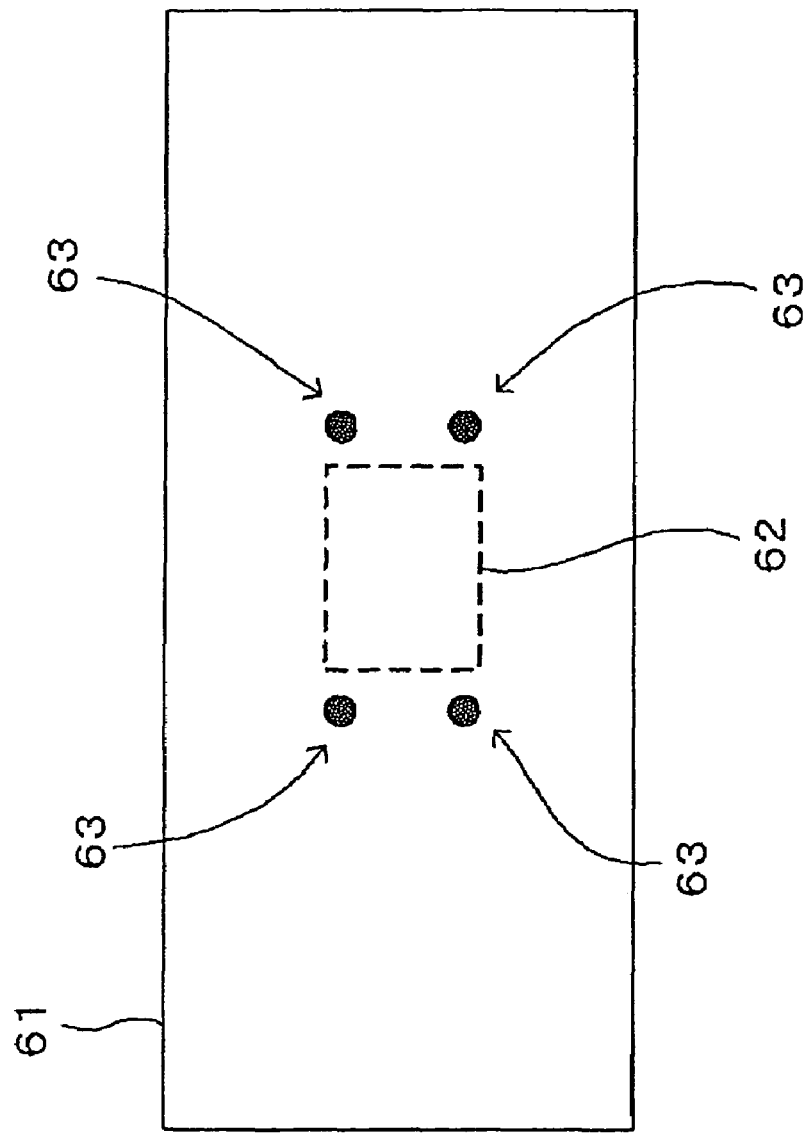
FIG. 1 is a plan view showing a configuration of a biochip according to the present embodiment.

FIG. 1 is a plan view showing a configuration of a biochip according to the present embodiment.

As shown in FIG. 1, a site area 62 is formed on a substrate 61 of a biochip 60. A plurality of sites are disposed in a matrix fashion on the site area 62. Four markers 63 are provided around the site area 62.

Respective sites on the site area 62 are formed by dripping spotted liquid such as a DNA solution and so forth. Further, respective markers 63 are formed by dripping opaque liquid by use of a device used for forming respective sites. Since the respective sites and the markers 63 are continuously formed by spotted liquid by use of the same device, a mutual positional relationship therebetween is defined with excellent accuracy. Once the positional relationship can be defined, a fabricating method is not limited. Opaque liquid is achieved by dyes, pigment or by bonding gold colloid to the DNA, or by bonding a coloring matter such as dyes or pigment to the DNA via biotin.

The substrate 61 is formed by use of, e.g. glass. The substrate 61 may be transparent or opaque by providing a metal layer on the surface thereof or reflective.

The markers 63 are formed so as to be recognized in their positions relative to the substrate 61 by a reflected light or transmitted light. A light reflectance or transmittance relative to an illuminated light, described later, may be differentiated between an area on which the markers 63 are formed and an area on which the markers 63 are not formed.

Figure 2:
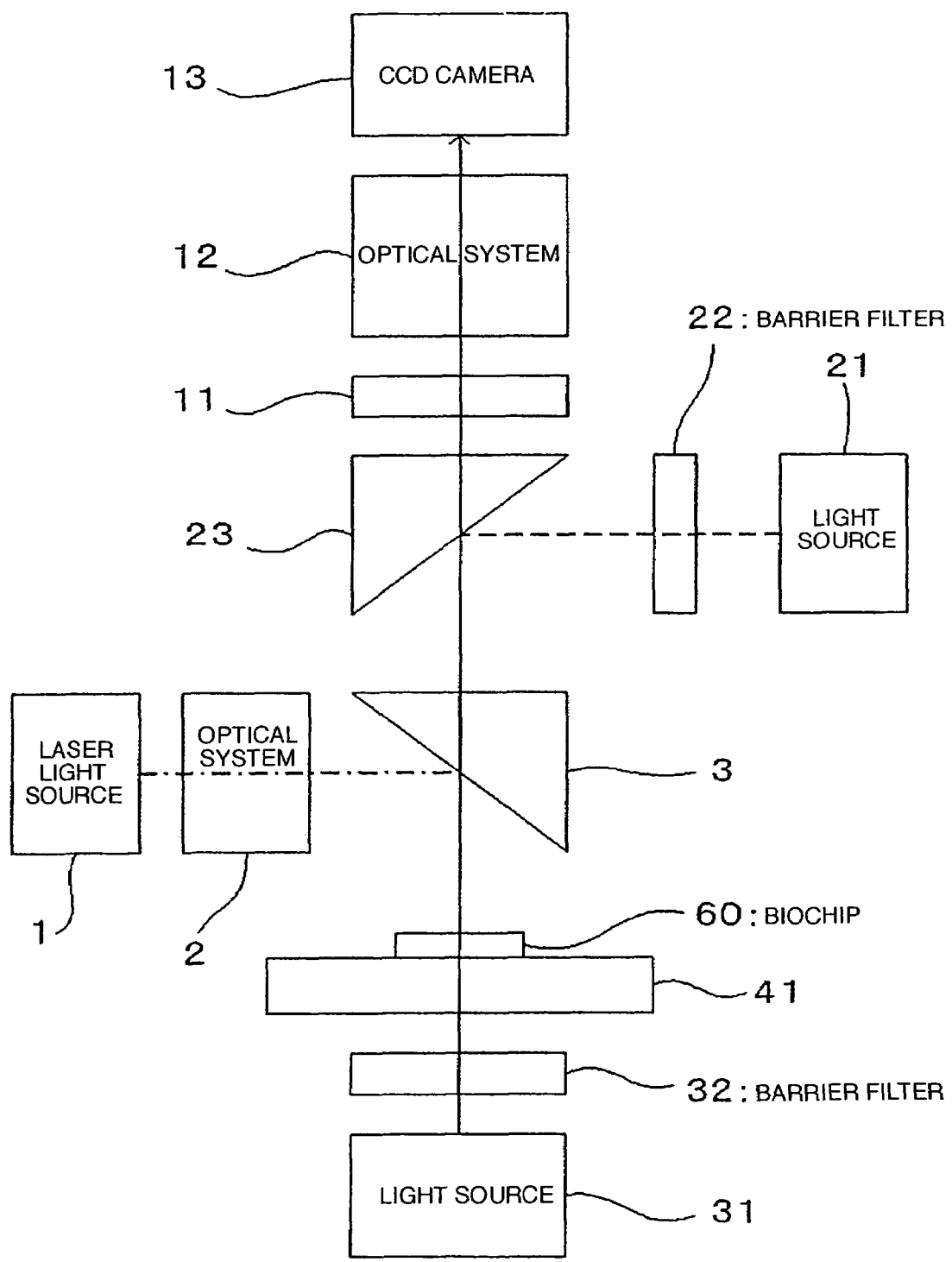
FIG. 2 is a view showing a configuration of an optical system of a biochip reader for reading the biochip according to the present embodiment.

FIG. 2 is a view showing a configuration of an optical system of a biochip reader for reading the biochip 60.

As shown in FIG. 2, the biochip reader of the present embodiment is provided with a laser light source 1 for generating excited light, an optical system 2, and a dichroic mirror 3 for bending laser light, as an optical system for illuminating excited light on the biochip 60.

A wavelength of the laser light source 1 conforms to the excited light of fluorescent molecules of cy3 or cy5.

Meanwhile, the biochip reader of the present embodiment is also provided with a barrier filter 11 and an optical system 12 disposed on a light pass, respectively, and a CCD camera 13 for receiving light which passed through the optical system 12, as an optical system for receiving light from the biochip 60.

Further, the biochip reader of the present embodiment is also provided with a light source 21 for outputting a white light, a barrier filter 22 and a dichroic mirror 23 for bending light from the light source 21, as an optical system for implementing illumination of reflected light. The barrier filter 22 has a function to eliminate a wavelength component of the excited light of fluorescent molecules among light outputted from the light source 21 or to allow only light having a wavelength longer than the excited light to pass therethrough. With this function, color fading of fluorescent light is prevented.

Still further, the biochip reader of the present embodiment is also provided with a light source 31 for outputting a white light and a barrier filter 32, as an optical system for implementing illumination of transmitted light. The barrier filter 32 has a function to eliminate a wavelength component of the excited light of fluorescent molecules among light outputted from the light source 31 or to allow light having a wavelength longer than the excited light to pass therethrough. With this function, color fading of fluorescent light is prevented.

As shown in FIG. 2, the biochip 60 is placed on a table 41.

FIG. 3 is a block diagram showing a configuration of a control system of the biochip reader according to the present embodiment.

As shown in FIG. 3, the biochip reader according to the present embodiment is provided with an arithmetic section 51 for executing various arithmetic operation, the laser light source 1, the light source 21, the light source 31, the CCD camera 13 and a controller 61 for controlling the arithmetic section 51.

A procedure for detecting positions of the sites on the biochip 60 is described next.

According to the present embodiment, the positions of the markers 63 are detected by use of the reflected light or transmitted light corresponding to the configuration of the biochip, and the position of the site area 62 can be recognized on the basis of the positions of the markers 63.

The light source 21 is actuated when the reflected light is used. The light from the light source 21 passes through the barrier filter 22 and is bent by the dichroic mirror 23, then passes through the dichroic mirror 3, and illuminates the biochip 60. The reflected light on the biochip 60 advances upward in FIG. 2, and is detected by the CCD camera 13. A signal outputted from the CCD camera 13 is sent to the arithmetic section 51, and the positions of the markers 63 on the biochip 60 are detected by the arithmetic section 51.

As mentioned above, since the positional relationship between the markers 63 and the site area 62 is defined according to the biochip of the invention, the position of the site area 62 can be recognized by the arithmetic section 51 on the basis of the positions of the markers 63.

The light source 31 is actuated when the transmitted light is used for detecting the positions of the sites. The light from the light source 31 passes through the barrier filter 32 and illuminates the biochip 60 from the table 41 side. The transmitted light advances upward in FIG. 2 like the reflected light as set forth above, and is detected by the CCD camera 13. A signal outputted from the CCD camera 13 is sent to the arithmetic section 51, and the positions of the sites on the biochip 60 are detected by the arithmetic part 51.

As mentioned above, since the positional relationship between the markers 63 and the site area 62 is defined according to the biochip of the invention, the position of the site area 62 can be recognized by the arithmetic section 51 on the basis of the positions of the markers 63.

The operation of the biochip 60 when measuring the biochip 60 is explained next.

When measuring the biochip 60, laser light outputted from the laser light source 1 passes through the optical system 2, and is bent by the dichroic mirror 3, then illuminates the biochip 60.

Fluorescent light from the biochip 60 generated by the excitation caused by the laser light passes through the dichroic mirror 3, the dichroic mirror 23, the barrier filter 11 and the optical system 12, and is detected by the CCD camera 13. The signal outputted from the CCD camera 13 is sent to the arithmetic section 51 and the quantities of light of respective sites on the biochip 60 are measured by the arithmetic section 51.

It is necessary to specify the position of respective sites in order to calculate the quantities of light of fluorescent light on respective sites. The positions of respective sites are first specified on the basis of image obtained by the CCD camera 13 in an image processing in accordance with the result of detection obtained by the above-mentioned procedure, then the quantities of light on that area are measured. As mentioned above, since the position of the site area 62 can be accurately recognized from the positions of the markers 63, the quantities of light of respective sites can be measure with excellent accuracy.

The positions of the markers 63 may be detected after the fluorescent light from the biochip 60 is taken in the CCD camera 13. The image taken in the CCD camera 13 is specified later on the basis of the result of detection of the positions of the markers 63, then the quantity of the fluorescent light can be measured.

According to the embodiment set forth above, the wavelength of the illuminated light is restricted in order to prevent the color fading of fluorescent light of the fluorescent molecules, it can be arbitrarily selected if the color fading of fluorescent light does not issue a problem.

Although the illuminated light is obtained by combining the white light source and the barrier filter, instead thereof, an LED, an electro-luminance or a laser light source and so forth can be used.

Further, objective biopolymer is not limited to DNA, but RNA, protein, sugar chain, bio-metabolites may be used.

The range of application of the invention is not limited to the present embodiment. The invention can be widely applied to a biochip for implementing analysis on the basis of the distribution of the quantity of fluorescent light generated at respective sites, and a situation for reading such a biochip.

What is claimed is:

1. A biochip reader for implementing analysis on the basis of the distribution of a quantity of light of fluorescent light generated at sites on a biochip, said reader comprising:
    marker position detecting means for detecting positions of markers formed on the biochip;
    site area recognition means for recognizing a site area on the basis of the positions of said markers;
    site position detecting means for detecting sites in said site area; and
    recognition means for recognizing positions of the sites on the biochip on the basis of the positions of the markers thus detected.

2. The biochip reader of claim 1, wherein the marker position detecting means is positioned above the biochip and detects by using reflected light and the site position detecting means is positioned below the biochip and detects by using transmitted light.

3. A biochip reading method for implementing analysis on the basis of the distribution of a quantity of light of fluorescent light generated at sites on a biochip, said method comprising the steps of:

detecting markers formed on the biochip;
recognizing a site area on the basis of the positions of said markers thus detected;
detecting sites in said site area; and
recognizing positions of the sites on the biochip on the basis of the positions of the markers thus detected.

* * * * *